US012636170B2

(12) United States Patent
Li et al.

(10) Patent No.: US 12,636,170 B2
(45) Date of Patent: May 26, 2026

(54) STENT SYSTEM AND VASCULAR STENT

(71) Applicant: SHENZHEN CHUANGXIN MEDICAL TECHNOLOGY CO., LTD., Shenzhen (CN)

(72) Inventors: Quande Li, Shenzhen (CN); Yucheng Peng, Shenzhen (CN); Chengming Su, Shenzhen (CN)

(73) Assignee: SHENZHEN CHUANGXIN MEDICAL TECHNOLOGY CO., LTD., Shenzhen (CN)

( * ) Notice: Subject to any disclaimer, the term of this patent is extended or adjusted under 35 U.S.C. 154(b) by 753 days.

(21) Appl. No.: 17/634,875

(22) PCT Filed: Nov. 11, 2020

(86) PCT No.: PCT/CN2020/128206
§ 371 (c)(1),
(2) Date: Feb. 11, 2022

(87) PCT Pub. No.: WO2021/120929
PCT Pub. Date: Jun. 24, 2021

(65) Prior Publication Data
US 2022/0304836 A1 Sep. 29, 2022

(30) Foreign Application Priority Data
Dec. 19, 2019 (CN) .......................... 201922295424.6

(51) Int. Cl.
*A61F 2/90* (2013.01)
*A61F 2/95* (2013.01)

(52) U.S. Cl.
CPC .................. *A61F 2/90* (2013.01); *A61F 2/95* (2013.01); *A61F 2210/0014* (2013.01); *A61F 2220/0008* (2013.01)

(58) Field of Classification Search
None
See application file for complete search history.

(56) References Cited

U.S. PATENT DOCUMENTS

| | | | | |
|---|---|---|---|---|
| 2003/0158594 A1* | 8/2003 | Kang | ........................ | A61F 2/95 623/1.13 |
| 2015/0148888 A1* | 5/2015 | Milner | ..................... | A61F 2/88 623/1.22 |

FOREIGN PATENT DOCUMENTS

| | | | |
|---|---|---|---|
| CN | 201445575 U | * 5/2010 | |
| CN | 105997298 A | 10/2016 | |

(Continued)

OTHER PUBLICATIONS

Supplementary Search Report for EP20901915, prepared by the European Patent Office, dated Jun. 5, 2023.

(Continued)

*Primary Examiner* — Javier G Blanco
(74) *Attorney, Agent, or Firm* — Brooks Kushman P.C.

(57) ABSTRACT

A vascular stent, which includes: a stent body including a plurality of ring-shaped units arranged at intervals and a connecting portion connecting all the ring-shaped units into a tubular structure, wherein the tubular structure has a first covered segment and a second covered segment that are provided with membrane, and an exposed segment configured for engaging the first covered segment and the second covered segment. The vascular stent is reliable in installation, which is beneficial to reduce pre-operation and post-operation adjustment work. The stent system can realize the reliable installation of the vascular stent, which is beneficial to improve the quality of the operation and reduce the operation time.

4 Claims, 6 Drawing Sheets

(56)         References Cited

FOREIGN PATENT DOCUMENTS

| | | | |
|----|------------|-----|---------|
| CN | 106983581  | A   | 7/2017  |
| CN | 108095858  | A   | 6/2018  |
| CN | 109481109  | A   | 3/2019  |
| CN | 109846585  | A   | 6/2019  |
| CN | 110151357  | A   | 8/2019  |
| CN | 211356087  | U   | 8/2020  |
| JP | 2005110778 | A * | 4/2005  |
| WO | 2005023149 | A2  | 3/2005  |
| WO | 2016210380 | A1  | 12/2016 |
| WO | 2018095090 | A1  | 5/2018  |

OTHER PUBLICATIONS

International Search Report for PCT Application No. PCT/CN2020/
128206, prepared by the China National Intellectual Property Admin-
istration, mailing date Jan. 27, 2021, 6 pages including English
Translation.

* cited by examiner

STENT SYSTEM AND VASCULAR STENT

CROSS-REFERENCE TO RELATED APPLICATION

This application is the U.S. national phase of PCT Application No. PCT/CN2020/128206 filed on Nov. 11, 2020, which claims priority to CN patent application No. 201922295424.6 filed on Dec. 19, 2019, the disclosures of which are incorporated in their entirety by reference herein.

TECHNICAL FIELD

The present application relates to the technical field of medical equipment, in particular to a stent system and a vascular stent.

BACKGROUND

In recent years, some scholars have begun to try to use endovascular exclusion to treat aortic diseases, and related chimney and fenestration techniques have begun to achieve some results, and the results are encouraging. However, due to the particularity of the anatomical structure of the aortic arch and the complexity of hemodynamics, coupled with the large elasticity of the traditional stent system, this type of surgery has a higher risk.

SUMMARY

Based on this, it is necessary to provide a stent system and a vascular stent, which can be installed reliably and can reduce the risk of damage to the vascular in the arch, which is beneficial to improve the quality of the operation and reduce the risk of the operation.

The technical solution as following:

In a first aspect, the present application provides a vascular stent, which includes a stent body including a plurality of ring-shaped units arranged at intervals and a connecting portion connecting all the ring-shaped units into a tubular structure, wherein the tubular structure comprises a first covered segment and a second covered segment that are provided with membrane, the stent body further comprises an exposed segment configured for engaging the first covered segment and the second covered segment, the exposed segment is woven by a preset metal wire, and the exposed segment, is provided with mesh holes and at least one keel-wire running through both ends of the exposed segment.

When the above-mentioned vascular stent is used, the vascular stent is delivered into the aorta. The first covered segment is arranged at the ascending aorta, and the exposed segment is arranged at the arch of the aorta without obstructing the communication between the aorta and the three branch arteries, and the second covered segment is arranged at the descending aorta; since the first and second covered segments can be covered with membrane, the membrane can be used to seal the rupture on the ascending aorta and/or descending aorta, and forming a fixing structure of the blood vessel stent, that is the two ends of the vascular stent can be fixed reliably. At this time, the exposed segment is made by a braiding process, which can naturally form multiple mesh holes (no fenestration process is required), which will help ensure the safety of the vascular arch and facilitate the communication between the aorta and the three branch arteries of the aortic arch, it is easy to fit the intima of the aorta and does not affect the branch blood flow, maintains the original blood flow stability of the aorta, and helps reduce the risk of damage to the blood vessel of the arch. At the same time, the design of the keel-wire increases the integrity of the vascular stent, so that the exposed segment has a certain torsion, which is more in line with the anatomical structure of the blood vessel, which is beneficial to improve the reliability of the fixation of the two ends of the vascular stent, and makes the installation of the vascular stent safe and reliable. It is helpful to improve the quality of operation and reduce the risk of operation. In addition, the foregoing analysis shows that the vascular stent of the present application can be applied to the ascending aorta, descending aorta, or ascending aorta and descending aorta for lesion closure, and has stronger applicability and, does not require fenestration process.

The technical solution is further explained below:

In one of embodiments, the keel-wire is woven around the preset metal wire.

In one of embodiments, the keel-wire is in a shape of a straight line, a broken line or a spiral line.

In one of embodiments, a material of the preset metal wire is Nitinol.

In one of embodiments, a length of the first covered segment is ranged from 10 mm to 90 mm, and a diameter of the first covered segment is ranged from 20 mm to 60 mm; or/and a length of the second covered segment is ranged from 10 mm to 300 mm, and a diameter of the second covered segment is ranged from 10 mm to 40 mm; or/and a length of the exposed segment is ranged from 40 mm to 200 mm, and a diameter of the exposed segment is ranged from 10 mm to 40 mm.

In another aspect, the present application further provides a stent system, including the vascular stent above mentioned, and further including a delivery device configured for delivering the vascular stent into an aorta.

The stent system uses the delivery device to deliver the corresponding vascular stent into the aorta.

When the above-mentioned vascular stent is used, the vascular stent is delivered into the aorta. The first covered segment is arranged at the ascending aorta, and the exposed segment is arranged at the arch of the aorta without obstructing the communication between the aorta and the three branch arteries, and the second covered segment is arranged at the descending aorta; since the first and second covered segments can be covered with membrane, the membrane can be used to seal the rupture on the ascending aorta and/or descending aorta, and forming a fixing structure of the blood vessel stent, that is the two ends of the vascular stent can be fixed reliably. At this time, the exposed segment is made, by a braiding process, which can naturally form multiple mesh holes (no fenestration process is required), which will help ensure the safety of the vascular arch and facilitate the communication between the aorta and the three branch arteries of the aortic arch, it is easy to fit the intima of the aorta and does not affect the branch blood flow, maintains the original blood flow stability of the aorta, and helps reduce the risk of damage to the blood vessel of the arch. At the same time, the design of the keel-wire increases the integrity of the vascular stent, so that the exposed segment has a certain torsion, which is more in line with the anatomical structure of the blood vessel, which is beneficial to improve the reliability of the fixation of the two ends of the vascular stent, and makes the installation of the vascular stent safe and reliable. It is helpful to improve the quality of operation and reduce the risk of operation. In addition, the foregoing analysis shows that the vascular stein of the present application can be applied to the ascending aorta, descending aorta, or ascending aorta and descending aorta for lesion closure, and has stronger applicability and does not require fenestration process the mesh holes.

The technical solution is further explained below:

In one of embodiments, the delivery device includes a delivery tube and a control mechanism, and the delivery tube comprises an introduction body provided at a free end of the delivery tube and, a first tube body and a second tube body that are configured for storing the vascular stent, the first tube body is able to be bent relative to the second tube body, and one end of the first tube body is detachably connected to the introduction body, and the other end of the first tube body is connected to one end of the second tube body, and the other end of the second tube body is arranged on the control mechanism, and the control mechanism comprises a first control portion configured for releasing the vascular stent, a second control, portion configured for controlling bending of the first tube body, and a first force applying portion configured for pushing or pulling out the delivery tube.

In one of embodiments, the second control portion includes a traction member and a second force applying portion movably disposed, and one end of the traction member is fixedly connected to the introduction body or/and the first tube body, and the other end of the traction member is fixedly connected to the second force applying portion.

In one of embodiments, the second force applying portion can be rotatably arranged or telescopically arranged.

In one of embodiments, the traction member and the second force applying portions corresponding to the traction members one-to-one are provided with at least two, and one end of at least one of the traction members is fixedly connected to the introduction body, and one end of at least one of the traction members is fixedly connected with the first tube body.

Figure 1:
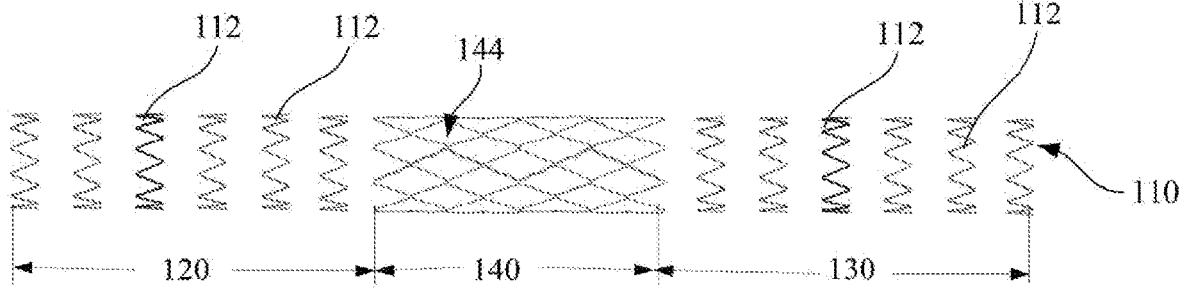
FIG. 1 is, a schematic structural view of a vascular stent in an embodiment.

The reference signs are listed:

100—vascular stent; 110—stent body; 112—ring-shaped unit; 120—first covered segment; 130—second covered segment; 140—exposed segment; 142—keel-wire; 144—mesh hole; 200—delivery device; 210—delivery tube; 212—introduction body; 214—first tube body; 216—second tube body; 220—control mechanism; 222—first control portion; 224—second control portion; 202—traction member; 204—second force applying portion; 226—first force applying portion; 228—post-release structure; 300—aorta; 310—ascending aorta; 320—arch; 330—descending aorta; 400—branch arteries.

DETAILED DESCRIPTION

In order to make the objectives, technical solutions, and advantages of the present, application clearer, the present application will be further described in detail below with reference to the accompanying drawings and specific embodiments. It should be understood that the specific embodiments described herein are only used to explain the present application, and do not limit the protection scope of the present application.

It should be noted that when an element is referred to as being "fixed to", "arranged on", "disposed on" or "installed on" another element, it can be directly on the other element or there may also be a centered element. When an element is considered to be "connected" to another element, it can be directly connected to the other element or an intermediate element may be present at the same time. Further, when one element is, regarded as a "fixed transmission connection" and, another element, the two can be fixed in a detachable connection or non-detachable connection, which can realize power transmission, such as sleeved connection and engagement, one-piece molding fixing, welding, etc., which can be realized in the prior art, and it is no longer burdensome here. When a component and another component are perpendicular or approximately perpendicular to each other, it means that the ideal state of the two is perpendicular, but due to the influence of manufacturing and assembly, there may, be a certain vertical error. The terms "vertical", "horizontal", "left", "right" and similar expressions used herein are for illustrative purposes only, and do not mean that they are the only embodiments.

Unless otherwise defined, all technical and scientific terms used herein have the same meaning as commonly understood by those skilled in the technical field of the present application. The terminology used in the specification of the present application herein is only for the purpose of describing specific embodiments, and is not intended to limit the present application. The term "and/or" as used herein includes any and all combinations of one or more related listed items.

The "first" and "second" involved in the present application do not represent specific quantities and sequences, but are only used to distinguish names.

Stanford Type A acute aortic dissection type A (referred to as AADA) is a catastrophic disease that severely endangers the patient's life and safety. It is characterized by sudden onset, rapid disease progression, and high mortality.

Figure 2:
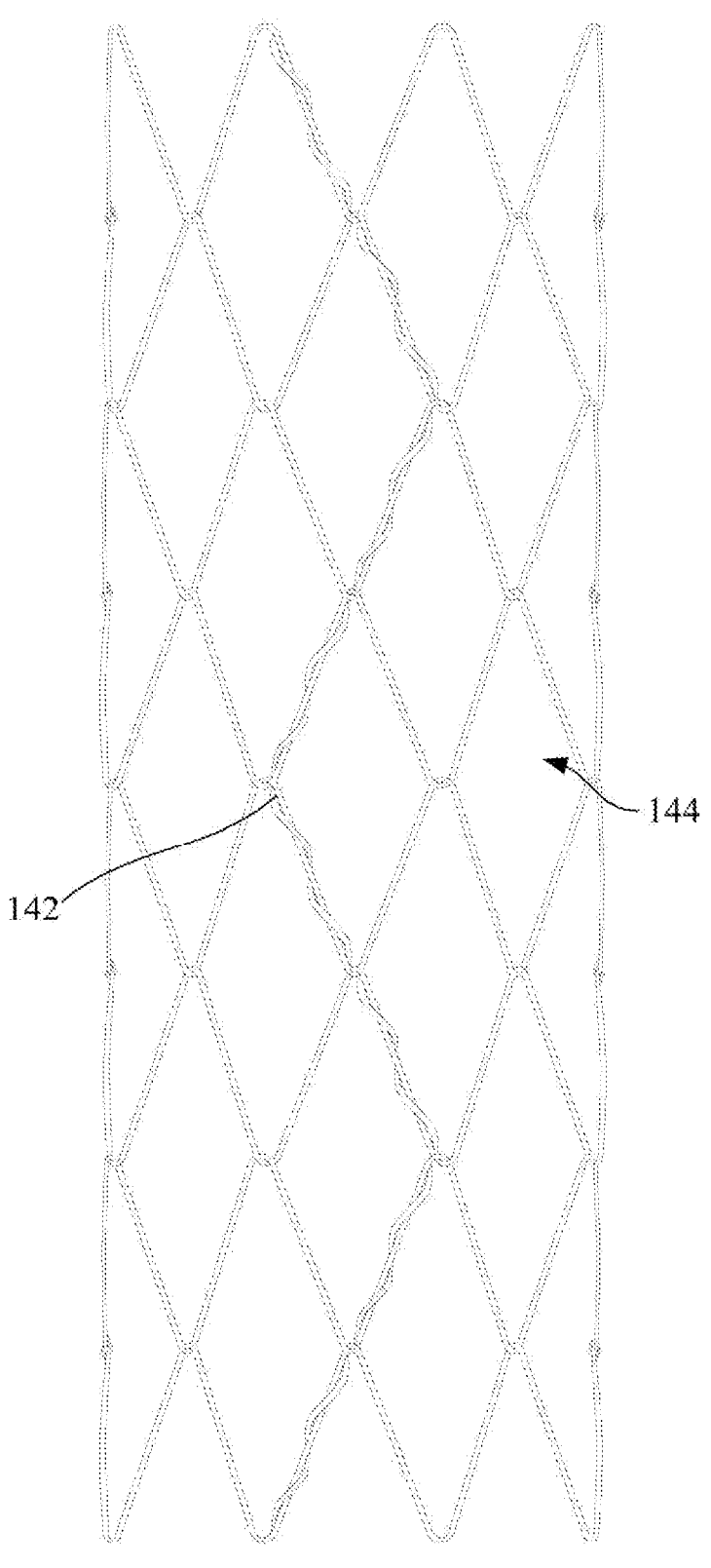
FIG. 2 is a schematic structural view of an exposed segment shown in FIG. 1.

As shown in FIG. 1 and FIG. 2, in one embodiment, a vascular stent 100 is provided, which includes a stent body 110. The stent body 110 includes a plurality of ring-shaped units 112 arranged at intervals, and all the ring-shaped units 112 are connected to each other to form a tubular structure. The tubular structure includes a first covered segment 120 and a second covered segment 130 provided with membrane. The stent body 110 also includes an exposed segment 140 that connects the first covered segment 120 and the second covered segment 130. The exposed segment 140 is woven by a preset metal wire, and the exposed segment 140 is provided with at least one keel-wire 142 running through both ends of the exposed segment 140.

Figure 3:
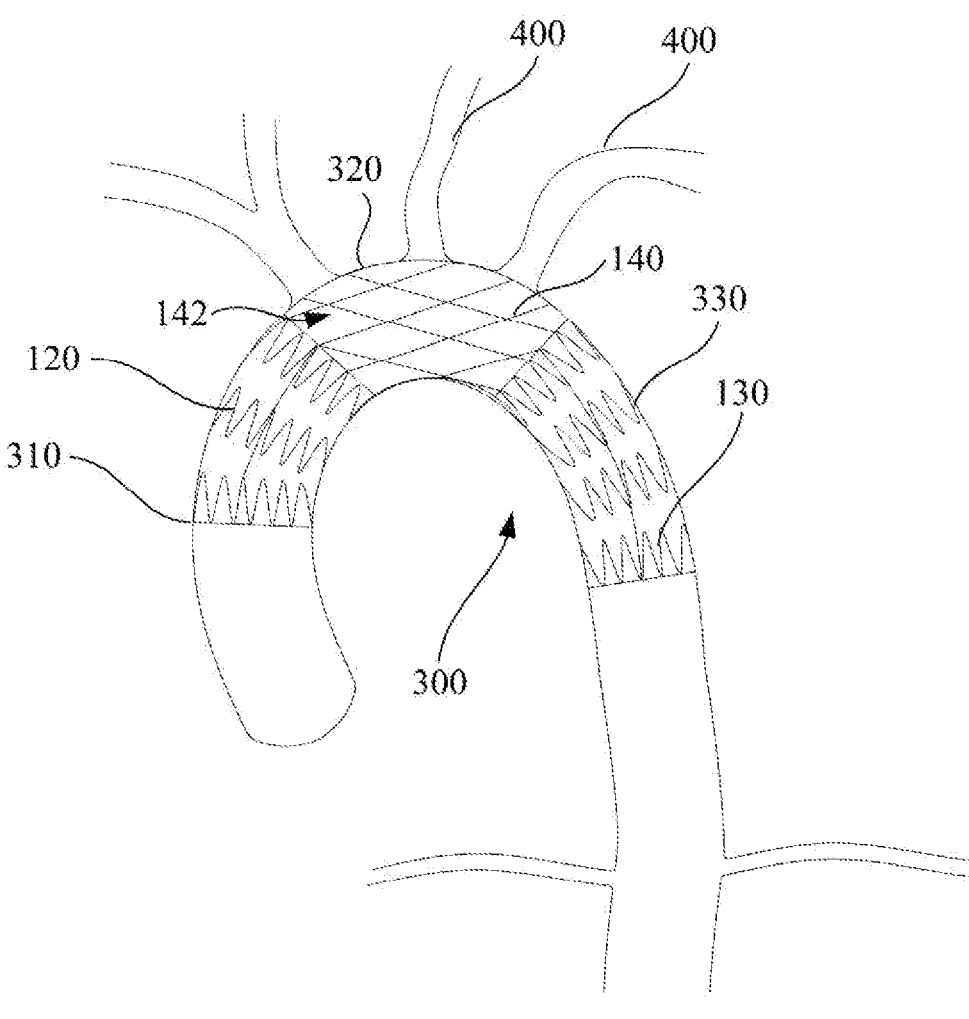
FIG. 3 is a schematic view of q vascular stent shown in FIG. 1 when it is applied to the treatment of Stanford A type aortic dissection disease.

As, shown in FIGS. 1 and 3, when the above-mentioned vascular stent 100 is applied to the treatment of Stanford Type A aortic dissection, the vascular stent 100 is delivered into the aorta 300. The first covered segment 120 is arranged at the ascending aorta 310, and the exposed segment 140 is arranged at the arch 320 of the aorta 300 without obstructing the communication between the aorta 300 and the three branch arteries 400, and the second covered segment 130 is arranged at the descending aorta 300; since the first and second covered segments 120, 130 can be covered with membrane, the membrane can be used to seal the rupture on the ascending aorta 310 and/or descending aorta 330, and forming a fixing structure of the blood vessel stent 100, that is the two ends of the vascular stent 100 can be fixed reliably. At this time, the exposed segment 140 is made by a braiding process, which can naturally form multiple mesh holes 144 (no fenestration process is required), which will help ensure the safety of the vascular arch and facilitate the communication between the aorta 300 and the three branch arteries 400 of the arch 320 of the aortic 300, it is easy to fit the intima of the aorta 300 and does not affect the branch blood flow, maintains the original blood flow stability of the aorta 300, and helps reduce the risk of damage to the blood vessel of the arch. At the same time, the design of the keel-wire increases the integrity of the vascular stent, so that the exposed segment has a certain torsion, which is more in line with the anatomical structure of the blood, vessel, which is beneficial to improve the reliability of the fixation of the two ends of the vascular stent 100, and makes the installation of the vascular stent safe and reliable. It is helpful to improve the quality of operation and reduce the risk of operation. In addition, the foregoing analysis shows that the vascular stent 100 of the present application can be applied to the ascending aorta 310, descending aorta 330, or ascending aorta 310 and descending aorta 330 for lesion closure, and has stronger applicability and does not require fenestration process.

It should be noted that the frame material of the aforementioned vascular stent 100 (that is, the ring-shaped units 112 and the connecting portion) can be made of any existing material that meets the requirements, such as Nitinol; the membrane material of the first covered segment 120 and the second covered segment 130 can be polytetrafluoroethylene and the like. During manufacturing, the first covered segment 120, the second covered segment 130, and the exposed segment 140 can be manufactured separately and then assembled together.

On the basis of the above-mentioned embodiments, as shown in FIG. 2, in one embodiment, the keel-wire is woven around a preset metal wire. In this way, the keel-wire can be more closely fitted or integrated into the exposed segment, so that the integrity of the exposed segment is better. At this time, the keel-wire can be woven before weaving the exposed segment, or after weaving.

On the basis of the above-mentioned embodiment, in one embodiment, the keel-wire is in the shape of a straight line, a broken line or a spiral line. In this way, the keel-wire can be designed according to the required torsion characteristics of the exposed segment, so that the exposed segment has better mechanical properties and is more in line with the characteristics of the vascular arch.

On the basis of the above-mentioned embodiment, in one embodiment, the material of the preset metal wire is Nitinol. In this way, the exposed segment 140 has better mechanical properties without affecting blood flow, in addition, the first covered segment 120, the exposed segment 140, and the second covered segment 130 and the exposed segment 140 may be connected by a connecting portion, or may be connected by membrane.

On the basis of any of the above-mentioned embodiments, as shown in FIGS. 1 and 3, in one embodiment, the connecting portion is a membrane connector or a metal connector. In this way, the first covered segment 120 and the second covered segment 130 can be directly connected to form a closed tube through a membrane connector, or a metal connector can connect multiple ring-shaped units 112 into a whole, and then be covered with membrane to form a closed tube. At this time, the exposed segment 140 can be connected to the tube through a metal connector; the first covered segment 120 and the second covered segment 130 have a blocking function, and the exposed segment 140 has a docking connection function, which is convenient for commercializing the vascular stent 100.

It should be noted that "top" refers to the position of the top of the aorta 300 after the vascular stent 100 is installed or preset; "two sides" refers to the position of the top of the aorta 300 after the vascular stent 100 is installed or preset, and corresponds to two sides of the top of the aorta 300, and not opposite to the "top" position.

On the basis of any of the above-mentioned embodiments, in one embodiment, the length of the first covered segment 120 is ranged from 10 mm~90 mm, and its diameter is ranged from 20 mm~60 mm; for example, the length is one selected from a group of 10 mm, 40 mm, 45 mm, 50 mm and 90 mm; the diameter is one selected from a group of 20 mm. 30 mm, 40 mm, 50 mm and 60 mm.

Further, in one embodiment, or/and the length of the second covered segment 130 is ranged from 10 mm~300 mm, and its diameter is ranged from 10 mm~40 mm; for example, the length is one selected from a group of 10 mm, 100 mm, 150 mm, 200 mm and 300 mm; the diameter is one selected from a group of 10 mm, 20 mm, 30 mm and 40 mm.

Further, in one embodiment, or/and the length of the exposed segment 140 is ranged from 40 mm to 200 mm, and the diameter thereof is ranged from 10 mm to 40 mm. For example, the length is one selected from a group of 40 mm, 90 mm, 100 mm, 120 mm and 200 mm; the diameter is one selected from a group of 10 mm, 20 mm, 30 mm and 40 mm.

In this way, it can be arranged according to actual requirements.

The specific structure of the ring-shaped units 112 can refer to the structure of any existing ring-shaped units 112 of the vascular stent 100. Specifically in the embodiment, the wave structure of the ring-shaped units 112 can be designed with different sine wave numbers, and the connection mode of one ring-shaped unit 112 and another ring-shaped unit 112 can be a peak-to-peak connection or a peak-to-trough connection.

On the basis of any of the above-mentioned embodiments, in one embodiment, the stent body 110 has a tapered structure as a whole.

Figure 4:
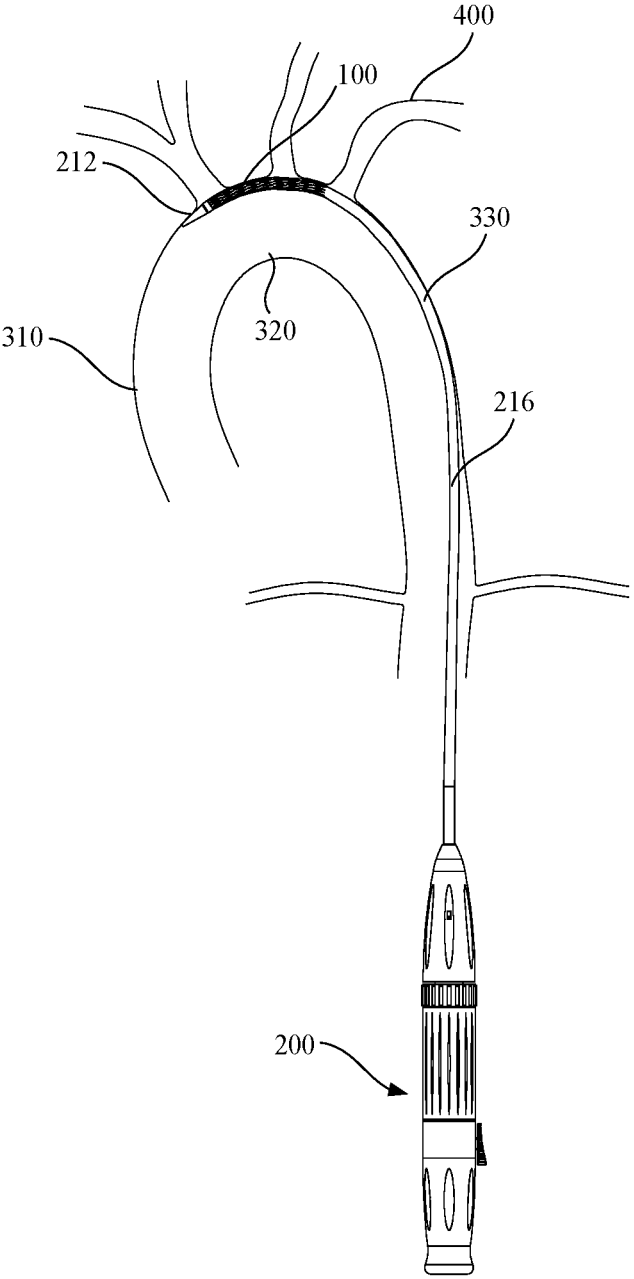
FIG. 4 is a schematic structural view of another embodiment of q stent system when it is applied to the treatment of Stanford A type aortic dissection disease.

In one embodiment, as shown in FIG. 4, a stent system is further provided, which includes the vascular stent 100 in any of the above embodiments, and further includes a delivery device 200, which is used to deliver the vascular stent 100 into the aorta 300.

As shown in FIGS. 3 and 4, when the stent system is applied to the treatment of Stanford Type A aortic dissection, the corresponding vascular stent 100 is delivered to the aorta 300 by the delivery device 200. The first covered segment 120 is arranged at the ascending aorta 310, and the exposed segment 140 is arranged at the arch 320 of the aorta 300 without obstructing the communication between the aorta 300 and the three branch arteries 400, and the second covered segment 130 is arranged at the descending aorta 300; since the first and second covered segments 120, 130 can be covered with membrane, the membrane can be used to seal the rupture on the ascending aorta 310 and/or descending aorta 330, and forming a fixing structure of the blood vessel stent 100, that is the two ends of the vascular stent 100 can be fixed reliably. At this time, the exposed segment 140 is made by a braiding process, which can naturally form multiple mesh holes 144 (no fenestration process is required), which will help ensure the safety of the vascular arch and facilitate the communication between the aorta 300 and the three branch arteries 400 of the arch 320 of the aortic 300, it is easy to fit the intima of the aorta 300 and does not affect the branch blood flow, maintains the original blood flow stability of the aorta 300, and helps reduce the risk of damage to the blood vessel of the arch. At the same time, the design of the keel-wire increases the integrity of the vascular stent, so that the exposed segment has a certain torsion, which is more, in line with the anatomical structure of the blood vessel, which is beneficial to improve the reliability of the fixation of the two ends of the vascular stent 100, and makes the installation of the vascular stent safe and reliable. It is helpful to improve the quality of operation and reduce the risk of operation. In addition, the foregoing analysis shows that the vascular stent 100 of the present application can be applied to the ascending aorta 310, descending aorta 330, or ascending aorta 310 and descending aorta 330 for lesion closure, and has stronger applicability and does not require fenestration process.

The specific structure of the above-mentioned delivery device 200 can be implemented with reference to the delivery device 200 disclosed in the prior art that can meet the delivery of the vascular stent 100.

Figure 5:
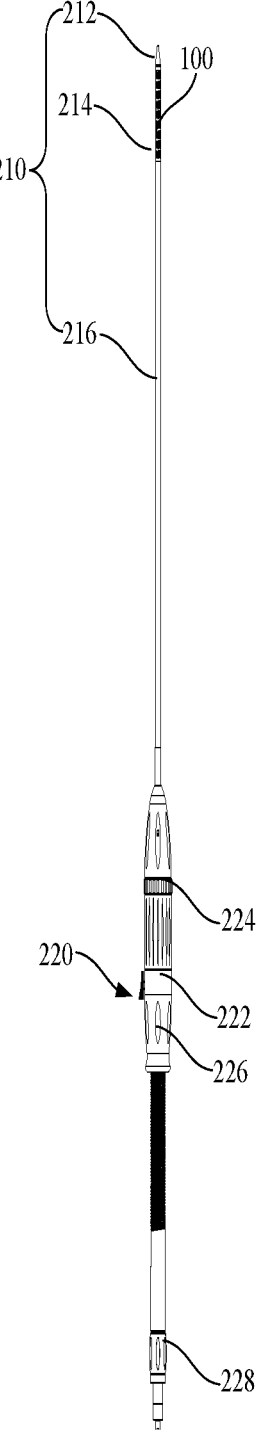
FIG. 5 is a schematic structural view of a delivery device shown in FIG. 4.

As shown in FIGS. 4 and 5, specifically in the embodiment, the present application provides a delivery device 200. The delivery device 200 includes a delivery tube 210 and a control mechanism 220. The delivery tube 210 includes an introduction body 212 disposed at the free end of the delivery tube 210, a first tube body 214 configured for storing the vascular stent 100, and a second tube body 216. The first tube body 214 can bend relative to the second tube body 216, and one end of the first tube body 214 is detachably connected with the introduction body 212. The other end of the first tube body 214 is connected to one end of the second tube body 216. The other end of the second tube body 216 is arranged on the control mechanism 220. The control mechanism 220 includes a first control portion 222 configured for releasing the vascular stent 100, a second control portion 224 configured for controlling the bending of the first tube body 214, and a first force applying portion 226 configured for pushing or pulling out the delivery tube 210. The introduction body 212 is used to introduce the first tube body 214, and the introduction body 212 cooperates with the first tube body 214 to form a storage cavity for the vascular stent 100, and the first control portion 222 is used to release the vascular stent 100. At the same time, the first tube body 214 that can be bent and the second control portion 224 used to control the first tube body 214 to be bent are used, when the delivery tube 210 enters the arch 320 of the aorta 300, the first tube body 214 can be bent such that the vascular stent 100 can smoothly and safely pass the arch 320 of the larger aorta 300 without damaging the aorta 300 and branch vessels; it can overcome the difficulty of the existing delivery device 200 to pass the arch 320 of the aorta 300 or the problem that the process of transporting the vascular stent 100 is easy to damage the arch 320 of aorta 300, which reduces the risk of operation.

Specifically, taking the same reference plane as a reference, the delivery tube 210 can be adjusted in a certain direction or in two opposite directions, and the angle of the adjustment is greater than 0 degree and less than or equal to 180 degrees.

The diameter of the delivery tube 210 can be designed according to actual requirements.

Specifically, in the embodiment, the introduction body 212 has a conical shape, and the head thereof has a spherical shape. Of course, the specific structure of the introduction body 212 can also refer to other existing structures.

In addition, the length of the introduction body 212 is ranged from 10 mm to 55 mm.

On the basis of the foregoing embodiment, as shown in FIGS. 4 to 7, in one embodiment, the second control portion 224 includes a traction member 202 and a second force applying portion 204 that can be movably arranged. One end of the traction member 202 is fixedly connected to the introduction body 212 or/and the first tube body 214, and the other end of the traction member 202 is fixedly connected to the second force applying portion 204. In this way, by moving the second force applying portion 204, the traction member 202 can contract, and then the introduction body 212 or the first tube body 214 can be stretched, such that the first tube body 214 can bend relative to the second tube body 216.

On the basis of the above-mentioned embodiment, in one embodiment, the second force applying portion 204 can be rotatably arranged or retractably arranged. Furthermore, the traction member 202 can be controlled by rotating or stretching. As shown in FIG. 5, specifically in this embodiment, the second force applying portion 204 can be rotatably arranged on the control mechanism 220.

On the basis of the first two embodiments, in one embodiment, the traction member 202 and the second force applying portion 204 corresponding to the traction member 202 are provided with at least two, one end of at least one traction member 202 is fixedly connected to the introduction body 212, and one end of at least one traction member 202 is fixedly connected to the first tube body 214. In this way, through at least two control points, the bending degree of the first tube body 214 can be controlled more finely, which can adapt to different arch types. For example, one of the second force applying portions 204 can be rotated to bend the first tube body firstly, and then when the first tube body is bent, the another second force applying portion 204 can be controlled to bend, such that the bending angle of the first tube body can be varied.

In addition, in one embodiment, the traction member 202 is a traction rope or a traction chain.

Figure 6:
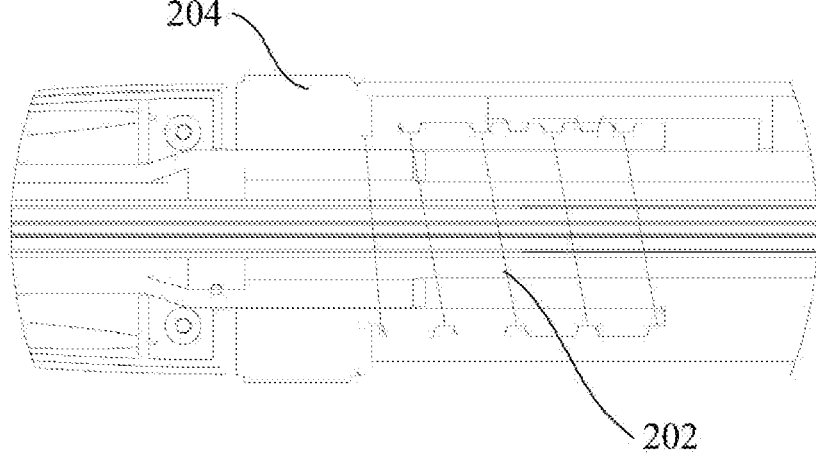
FIG. 6 is a schematic structural view of a second control portion of a partial cross-segmental view of a delivery device shown in an embodiment.
Figure 7:
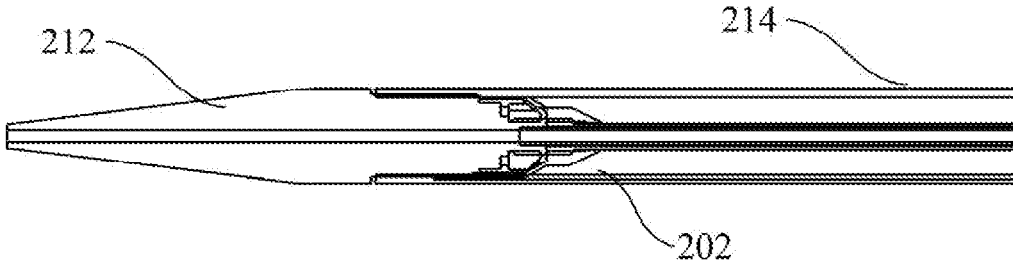
FIG. 7 is a schematic assembled view of a traction member and the introduction body of a partial cross-segmental view of a delivery device shown in an embodiment.

Specifically in the embodiment, as shown in FIGS. 6 and 7, the traction member 202 is a traction rope, which is beneficial to save space, so that the volume of the delivery device can be smaller, especially the volume of the delivery tube is smaller, which is suitable for micro invasive surgery.

Of course, the aforementioned delivery device 200 can also be provided with a post-release structure 228.

The above-mentioned stem system can be applied to minimally invasive treatment, which is beneficial to reduce the patient's pain and surgical risk. At the same time, the improvement of vascular stent 100 can greatly shorten the operation time of the doctor and increase the probability of saving lives. At the same time, the structure of the vascular stent 100 and the structure of the adjustable delivery tube 210 ensure the safety, effectiveness and convenience of the product in use.

The technical features of the above embodiments can be combined arbitrarily. In order to make the description concise, all possible combinations of the technical features in the above embodiments are not described. However, as long as the combinations of these technical features are not contradictory, they should be considered as the range described in the specification.

The above examples only express several implementations of the present application, and the description is relatively specific and detailed, but it should not be understood as a limitation on the scope of the present application. It should be pointed out that for those skilled in the art, without departing from the concept of the present application, several modifications and improvements can be made, and these all fall within the protection scope of the present application. Therefore, the protection scope of the present application should be subject to the appended claims.

What is claimed is:

1. A vascular stent, comprising:

a stent body, comprising a plurality of ring-shaped units arranged at intervals and a connecting portion connecting all the ring-shaped units into a tubular structure, wherein the tubular structure comprises a first covered tubular segment and a second covered tubular segment that are provided with membrane, the stent body further comprises an uncovered, exposed tubular segment having an end engaging an end of the first covered tubular segment and an opposite end engaging an end of the second covered tubular segment, the exposed tubular segment is woven by a preset metal wire, and the exposed tubular segment is provided with mesh holes and at least one keel-wire running through the two ends of the exposed tubular segment;

wherein the keel-wire is woven around the preset metal wire by twisting along straight sections of the preset metal wire, and the keel-wire is extended in a zig-zag pattern along an axis direction of the exposed tubular segment;

wherein the first covered tubular segment, the second covered tubular segment, and the exposed tubular segment are separate components that are assembled together;

wherein the first covered tubular segment is sized and configured to be arranged at the ascending aorta, the exposed tubular segment is sized and configured to be arranged at the arch of the aorta, and the second covered tubular segment is sized and configured to be arranged at the descending aorta; and wherein the keel-wire increases the integrity of the vascular stent, and it is designed according to a required torsion characteristic of the exposed tubular segment.

2. The vascular stent according to claim 1, wherein a material of the preset metal wire is Nitinol.

3. The vascular stent according to claim 2, wherein a length of the first covered tubular segment is ranged from 10 mm to 90 mm, and a diameter of the first covered tubular segment is ranged from 20 mm to 60 mm; or/and a length of the second covered tubular segment is ranged from 10 mm to 300 mm, and a diameter of the second covered tubular segment is ranged from 10 mm to 40 mm; or/and a length of the exposed tubular segment is ranged from 40 mm to 200 mm, and a diameter of the exposed tubular segment is ranged from 10 mm to 40 mm.

4. The vascular stent according to claim 1, wherein a length of the first covered tubular segment is ranged from 10 mm to 90 mm, and a diameter of the first covered tubular segment is ranged from 20 mm to 60 mm; or/and a length of the second covered tubular segment is ranged from 10 mm to 300 mm, and a diameter of the second covered tubular segment is ranged from 10 mm to 40 mm; or/and a length of the exposed tubular segment is ranged from 40 mm to 200 mm, and a diameter of the exposed tubular segment is ranged from 10 mm to 40 mm.

* * * * *